United States Patent [19]

Oganesyan et al.

[11] 4,100,919
[45] Jul. 18, 1978

[54] APPARATUS FOR SURGICAL TREATMENT OF BONES AND JOINTS

[75] Inventors: Oganes Vardanovich Oganesyan; Nikolai Ivanovich Pyanov, both of Moscow, U.S.S.R.

[73] Assignee: Tsentralny Nauchno-Issledovatelsky Institut Travmatologii I Ortopedii Imeni N.N. Priorova, U.S.S.R.

[21] Appl. No.: 748,753

[22] Filed: Dec. 8, 1976

[51] Int. Cl.² .............................................. A61F 5/04
[52] U.S. Cl. ................................ 128/84 B; 128/92 A
[58] Field of Search ................ 128/84 B, 84 R, 92 A, 128/92 R, 92 B, 92 E

[56] References Cited

U.S. PATENT DOCUMENTS

| 2,406,987 | 9/1946 | Anderson | 128/92 A |
| 2,497,626 | 2/1950 | Persall | 128/92 A |
| 3,941,123 | 3/1976 | Volkov et al. | 128/84 B |
| 3,976,061 | 8/1976 | Volkov et al. | 128/84 B |
| 3,985,127 | 10/1976 | Volkov et al. | 128/92 A X |

Primary Examiner—John D. Yasko
Attorney, Agent, or Firm—Steinberg & Blake

[57] ABSTRACT

An apparatus, comprising a supporting and a rotatable stirrup together with respective wire spokes, intended for being drawn through juxtapositional bones and joints, forms two rigid systems. Said rigid systems are joined together by means of distractors with hinge joint fastenings, situated at the two ends of the wire spoke of the supporting stirrup. The position of the fulcrums of the hinge joints determines the position of the apparatus' axis of rotation. A special regulator is provided for adjusting the position of the axis of rotation of the apparatus which comprises a means for rotating the fulcrum of the hinge joint fastening the distractors and a means for moving the fulcrums of the hinge joints along the distractors connecting the supporting and rotatable stirrups.

10 Claims, 10 Drawing Figures

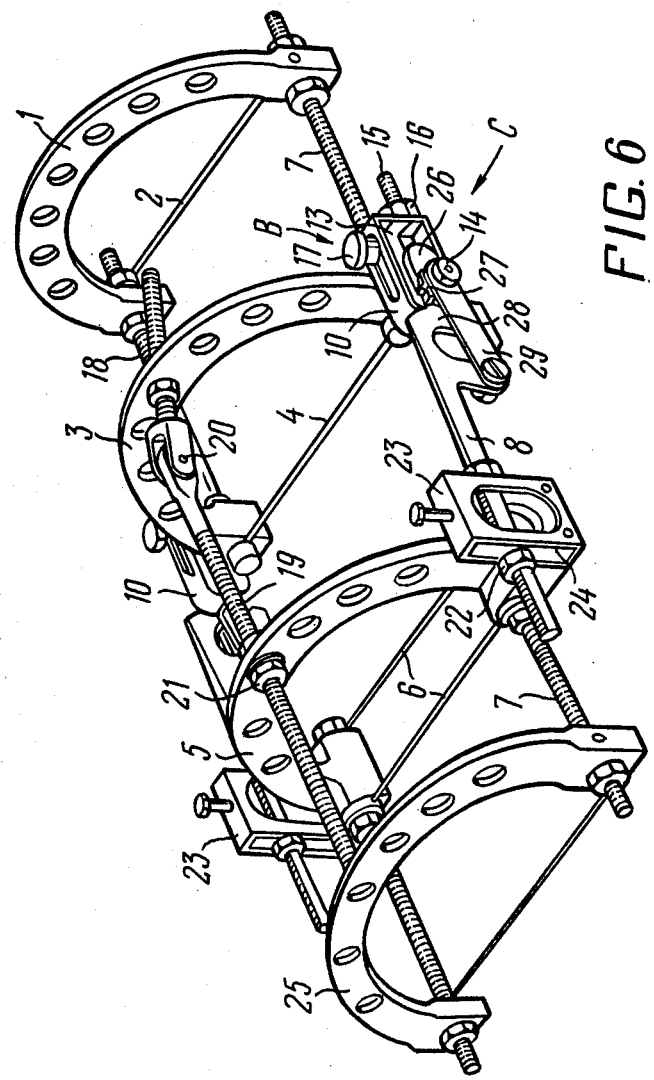

APPARATUS FOR SURGICAL TREATMENT OF BONES AND JOINTS

This invention relates to medical equipment, and more specifically to an apparatus for the surgical treatment of bones and joints. The proposed apparatus can be used in orthopedics and traumatology for reducing recent irreducible and old dislocations of, for example, the bones of the forearm, for osteosynthesis of recent intra-articular fractures with simultaneous restoration of movement by the affected joint.

Widely known in the art of surgical treatment of joints are apparatus including at least two pairs of wire spokes. The wire spoke ends of each pair are fastened in one or two stirrups, rigidly connected one with the other, so that each pair of wire spokes with the stirrups form a rigid system. The wire spokes of each rigid system are drawn through one of the juxtaposed bones. The rigid systems are connected one with the other by means of distractors allowing to alter the distance between these systems. The distractors are fastened, with their one end, to a rigid system rigidly, and to another, through a hinge joint allowing to change the mutual angular arrangement of the systems and, thereby, to imitate the movement of the patient's joint. For example, known in the art is an apparatus for the surgical treatment of monocentric joints (cf. USSR Inventor's Certificate No. 247,455), comprising three stirrups accommodating in their bases clamps for the fixation of a pair of wire spokes. The stirrup that fixes by means of wire spokes the movable part of the extremity is called the rotatable one, another stirrup, usually referred to as the supporting stirrup, serves to secure by means of an axial wire spoke the other, articular end of the bone, through which passes the joint's axis of rotation, for instance, through the epicondyles of the distal end of the humerus. And, in the ideal case, the axial wire spoke should pass along the axis of rotation of the patient's joint and serves as the fulcrum for the aforementioned hinge joint. The wire securing the bone at some distance from the joint is called the closing one. The closing and the supporting stirrups are rigidly interconnected by straight distractors, while the supporting and the rotatable ones, by hinge distractors whose one ends are rigidly fastened on the rotatable stirrup and the others are hinged to the supporting stirrup of the apparatus. The tops of the supporting and rotatable stirrups are connected by means of a flexion-extension device intended for changing the relative angle of rotation of the apparatus's stirrups.

Such an apparatus is applied to an extremity in the following way: the axial wire spoke is drawn through the articular end strictly along the axis of rotation of the joint, which passes in its main plane of movement. After the axial wire spoke has been inserted, the supporting stirrup of the apparatus is applied and the axial spoke therein is pulled up and fastened. The subsequent wire spokes are drawn, in turn, through the other parts of the extremity in accordance with the arrangement of the apparatus' stirrups, after which the wire spokes are pulled up and fastened.

After the apparatus has been applied, the distance between the supporting and rotatable stirrups is varied by moving the distractors, thereby setting a clearance of a preset magnitude between the articular ends, and the flexion-extension device is manipulated for gradually changing the angle of rotation of the rotatable stirrup with its wire spokes relative to the supporting stirrup, thereby exercising the articulation by movement.

One of the most complicated surgical tasks, however, is drawing the axial wire spoke of the apparatus' supporting stirrup precisely along the joint's axis of rotation. A deviation of the passing wire spoke from the true position of the joint's axis of rotation, in functional treatment, leads to hyperdistension of the ligaments, destruction of the articular cartilage due to the premature joining of the articular ends when exercising the patient's joint and, at the same time, it is extremely difficult for the surgeon to determine, while inserting the wire spoke, the true position of the joint's axis of rotation, particularly if one bears in mind that this position differs from patient to patient and from joint to joint.

It is an object of the invention to provide an apparatus for the surgical treatment of bones and joints, in which the axis of rotation is independent of the position of the axial wire spoke of the apparatus' supporting stirrup.

Another object of the invention is to provide the possibility of adjusting the position of the axis of rotation of the apparatus relative to the axis of rotation of the patient's joint.

Still another object of the invention is to reduce the painfulness and preclude injury to the articular cartilage and the soft-tissue elements of the joint.

These and other objects are attained by an apparatus for the surgical treatment of bones and joints, comprising at least a supporting and a rotatable stirrup, fastened in each of which are at least two pairs of wire spokes intended for being drawn through juxtapositional segments of bones or joints and forming two rigid systems, whose stirrups are connected one with another by distractors provided with hinge joints situated at the two ends of the wire spokes of the supporting stirrup and determining the position of the apparatus' axis of rotation, in accordance with the invention, is a regulator of the position of the apparatus' axis of rotation, including a means for rotating the fulcrum of each hinge joint fastening the distractor along a circumference relative to the wire spoke of the supporting stirrup, and a means for moving the fulcrums of the hinge joints along the distractors connecting the supporting and rotatable stirrups.

Such an embodiment of the apparatus provides for the position of the apparatus' axis of rotation, which must coincide with the true position of the axis of rotation of the patient's joint, being independent of the position of the wire spoke relative to said axis of the joint, and also for the possibility of adjusting the position of the axis of rotation of the apparatus relative to the axis of the joint, thereby precluding the destruction of the articular cartilage, the hyperdistension of the ligaments and other untoward physical effects on the patient, stemming from failure on the part of the axis of rotation of the apparatus to coincide with that of the patient's joint.

In one of the embodiments of the apparatus, the means for rotating the fulcrum of the hinge joint is provided by a rotatable pin whose axis of rotation is parallel to the axis of the wire spoke of the supporting stirrup, and which carries the fulcrum of the hinge joint, and a disc for the pin's movement in the slide slots along the axis of the distractor connecting the rigid system.

In the presence of such a rotatable pin, it either has a head, made flush with a disc rigidly connected with said pin and having an aperture for fitting therein the fulcrum of the hinge joint, or rigidly connected with the pin is a rod situated in the plane of rotation of the distractor connecting the supporting and rotatable stirrups, and the hinge joint fulcrum is secured thereon.

It is expedient that a lead screw be connected with the pin for moving it in the guide slot along the distractors connecting the supporting and rotatable stirrups of the rigid systems, and that a screw and lever-type clamp be provided for securing the pin in the desired position following its movement.

The disc may have several apertures situated radially at different distances from the pin's axis of rotation so that the radius of rotation of the hinge joint fulcrum can be altered relative to the wire spoke, depending on the radius of the surfaces of the segments being juxtaposed.

In another embodiment, the rod has several apertures arranged at different distances from the pin's axis of rotation for altering the radius of rotation of the hinge fulcrum relative to the wire spoke, depending on the radius of the surfaces of the segments being juxtaposed.

It is expedient that a circular guide connected with the supporting stirrup be provided in the apparatus, whose center coincides with the axis of the wire spoke of the supporting stirrup, and that set movably in this guide be a pin rotatable about its own axis and carrying a rod rigidly fastened thereto, situated in the plane of the distractor connecting the supporting and rotatable stirrups through apertures provided therein for mounting therein the fulcrum of the hinge joint of the distractors.

Still another embodiment of the apparatus has a circular guide, whose center coincides with the axis of the wire spoke of the supporting stirrup, and set therein rotatably about its own axis is a pin, carrying a rod rigidly connected thereto, and provided with an aperture for securing the hinge joint fulcrum, said guide being rotatable about its own axis, while said rod may have a number of apertures for setting the pin at different distances from the circular guide's center.

The invention will now be described with reference to preferred embodiments thereof, taken in conjunction with accompanying drawings, wherein:

FIG. 6 is a perspective view of another embodiment of the apparatus, in accordance with the invention;

Figure 1:
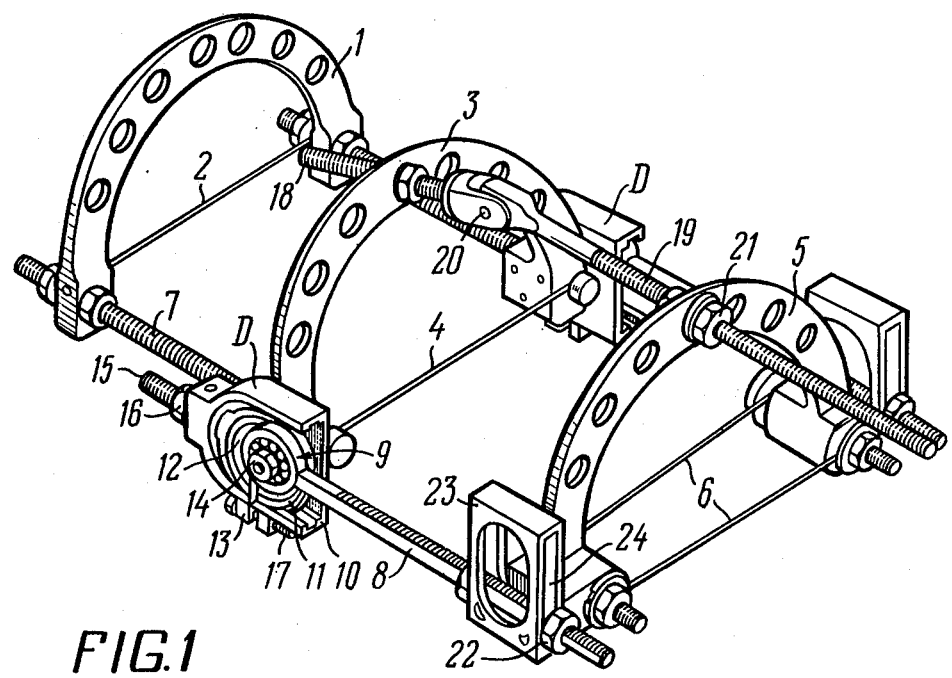
FIG. 1 is a perspective view of one of the embodiments of the apparatus, in accordance with the invention.

Referring now to the drawings, FIG. 1 is a general view of an apparatus for the surgical treatment of bones and joints, comprising a closing stirrup 1 with a wire spoke 2, a supporting stirrup 3 with an axial wire spoke 4, and a rotatable stirrup 5 with wire spokes 6. The closing stirrup 1 and the supporting stirrup 3 are connected one with the other by straight distractors 7 so that the stirrups, wire spokes and distractors form a rigid system, while the stirrup 5 together with the spokes 6 belonging thereto also form a rigid system. The rigid system comprising the stirrups 1 and 3, and the rigid system containing the stirrup 5 with the spokes 6, are connected one to the other by distractors 8, which are each provided with a hinge joint 9. In the simplest case, a hinge joint is essentially a fulcrum with a distractor mounted thereon by means of antifriction bearings. The geometric axis passing through the centers of the hinge joints 9, i.e. the axes of the antifriction bearings on which the distractors 8 are secured (FIG. 1 shows one hinge joint only), determines the position of the apparatus' axis of rotation and must coincide with the axis of rotation of the patient's joint, which is achieved by means of the present invention and will be outlined in detail below. The position of the axis of rotation of the apparatus is adjusted by means of two special similarly made devices situated at the two ends of the wire spoke of the apparatus' supporting stirrup. For simplicity, we shall consider only one such means.

Figure 2:
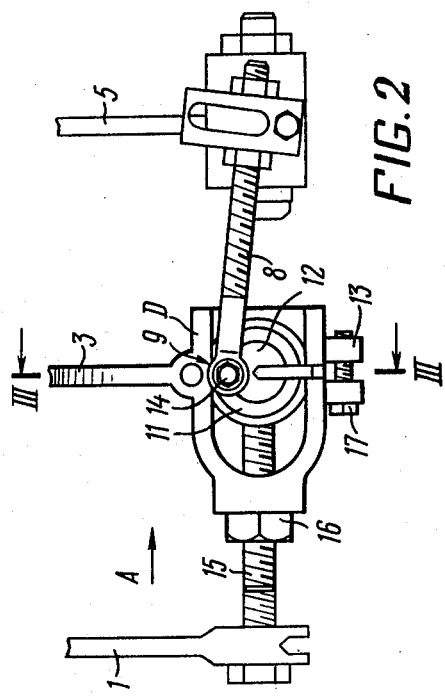
FIG. 2 shows the portion where the hinge joint fastening the distractor is mounted on the apparatus of FIG. 1.
Figure 5:
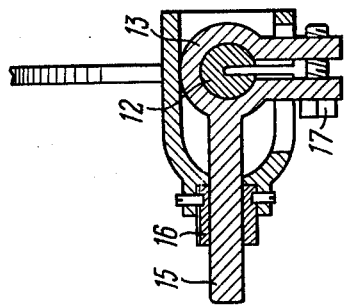
FIG. 5 is a sectional view taken along line Y—Y of FIG. 4.
Figure 3:
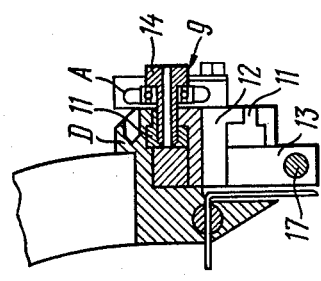
FIG. 3 is a sectional view taken along line III—III of FIG. 2.
Figure 4:
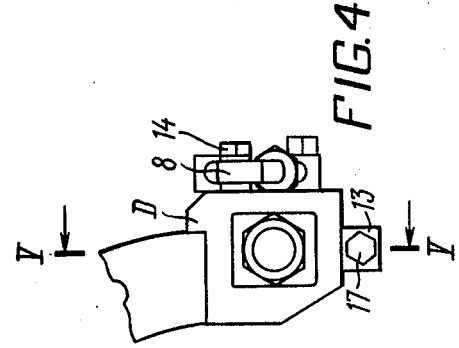
FIG. 4 is a view taken along arrow A of FIG. 2.

This means (FIGS. 2 and 3) includes a shell D rigidly fastened on the end of the stirrup 3 and provided with guide channels 10. Placed inside the shell D is a disc 11, with a pin 12 set flush therein and rotatable about its own axis, its end inserted in an aperture of a screw-and-lever-type clamp 13 (clearly shown in FIG. 5). Here, the axis of the pin 12 is situated parallel to the axis of the wire spoke 4 and may be coaxial therewith in the process of adjusting the apparatus, provided said wire spoke passes precisely through the center of rotation of the joint. For mounting the fulcrum 14 of the hinge joint 9 a hole is made on the outer side of the disc 11 on its border with the head of the pin 12. The disc 11 and the pin 12 are rigidly connected one with the other by means of the fulcrum 14 to provide for the latter's rotation about the axis of the pin 12 and, thereby, about the axial wire spoke 4 of the supporting stirrup 3, during the angular rotation of the pin 12. In order to provide for the longitudinal movement of the fulcrum 14 of the hinge joint 9 of the distractor 8, a hole is made in the rear part of the shell D through which passes one end of a lead screw 15 with a nut 16 (FIGS. 4 and 5). The other end of the lead screw 15 is made in the form of a screw-and-lever-type clamp 13, securing the pin 12 and actuated by means of a screw 17. The provision of the lead screw 15 with the screw-and-lever-type clamp 13 and the rotatable pin 12 allows changing the position of the fulcrum 14 and at the same time moving it longitudinally, and, consequently, adjusting the position of the apparatus' axis of rotation relative to the true position of that of the patient's joint. The tops or crests of the stirrups 3 and 5 are connected by means of a flexion-extension device, which essentially comprises two rods 18 and 19, linked with each other by a pin 20. The stirrups 3 and 5 are secured in position with nuts 21 of the flexion-extension device. The distractor 8 is fastened to the rotatable stirrup 5 by means of nuts 22 and a housing 23 with slots 24, through which passes the distractor 8. The end of the distractor 8 passing through the slots 24 of the housing 23 is threaded so that by rotating the nuts 22 it is possible to change the distance between the supporting and rotatable stirrups.

The application of the apparatus is started by drawing the wire spokes through the articular ends of the extremity. Here the axial wire spoke 4 is drawn along the axis of rotation of the patient's joint. The other wire spokes are drawn in the same way as in other apparatus well known to those skilled in the art. As has already been mentioned, the surgeon is practically unable to achieve the precise coincidence of the axial wire spoke of the apparatus with the true axis of rotation of the joint, owing to the absence of projection reference points and its topography, due to variations in the joint structure and the specific features of their individual development. When using the proposed invention, the surgeon, without excessively concentrating on the accuracy of drawing the axial wire spoke through the joint, has the possibility of subsequently aligning the axis of rotation of the apparatus with that of the patient's joint after is application. This is achieved by means of the pin 12 and the screw and lever-type clamp 13.

In cases where the axis of rotation of the hinge of the apparatus and that of the patient's joint fail to coincide, the pin 12 is rotated, which causes simultaneous rotation of the hinge joint fulcrum relative to the frontal plane of the extremity. This rotation is continued until the fulcrum of the hinge is brought into the plane of the projection of the axis of rotation of the patient's joint, and then, by means of the lead screw 15 and the nut 16, the screw and lever-type clamp 13 is put in motion together with the pin 12 and, consequently, moved together therewith is the fulcrum of the hinge until it has complete coincidence with the axis of rotation of the patient's joint. The topography of the joint's axis of rotation is reckoned with the aid of X-ray pictures after the application of the apparatus. After the hinge fulcrum is adjusted the pin is secured in the screw and lever-type clamp by means of the screw 17.

Following the final correction of the axes of rotation of the apparatus and the joint, a 4–5 mm diastasis is established between the articular ends by means of the nuts 22 of the distractors 8. Then, by means of the flexion-extension device 20, the position of the extremity is started to be altered by gradually changing the angle of rotation of the stirrup 5 and the distractor 8 in relation to the apparatus' supporting stirrup. Upon reaching an angle of 60°–70° another X-ray of the joint is taken. If one sees a diminished or expanded articular slit, the actual position of the joint's axis of rotation is estimated therefrom and the final adjustment of the hinge fulcrum is made after slightly releasing the screw 17 of the screw and lever type clamp 13, and then by an angular rotation and longitudinal motion of the hinge a precise coincidence of the axes of rotation of the apparatus and the patient's joint is attained. Then, the screw is tightened up again. Thus, after the axis of rotation of the apparatus' hinge is brought into coincidence with the true position of the axis of rotation of the patient's joint, the latter can now be exercised in accordance with its kinematics without causing anatomical destruction of its cartilage and soft-tissue elements, which is conducive to the restoration of the joint's functions in a shorter time.

In addition to the above function, the apparatus can also be used for removing angular diaphysary deformations in the case of flase joints and the retarded union of fractured long tubular bones. In this case, the axial wire spoke is drawn close to the apex of the angular deformation in direct proximity to the fracture, perpendicularly to its triangular projection. The other wire spokes are drawn in the same plane, their ends being fastened in the stirrups of the apparatus. By longitudinal and angular movement of the hinge it is arranged above the projection of the apex of the false joint and fastened in the set position.

After fastening, the removal of the angular deformation is started by a slight traction of the fractured portions and by gradually changing, by means of the flexion-extension device, the angle of rotation of the rotatable stirrup 5 and the distractors 8 in relation to the stirrup 3. Upon correcting the deformation the apparatus is locked in the position of a slight compression until the set position is stabilized by the callus. If, upon loosening the nuts of the flexion device 20 the fractured portions do not deflect from the normal axis of the extremity, one should consider the task achieved, with the possibility of going over to other kinds of immobilization, or of continuing it in the apparatus.

It must be borne in mind, that with a view to using the apparatus for the treatment of bones and joints having different radii of the surfaces of the segments being juxtaposed, there may be several apertures provided in the disc for setting the hinge fulcrum, and situated at different radial distances from the pin.

FIG. 6 is a general view of another embodiment of the apparatus in which the hinge joint of the distractor is fastened in a different way from that of FIG. 1. The elements similar to those of FIGS. 1 to 5 are not considered in detail and have the same reference numbers as those already mentioned.

Figures 7, 8:
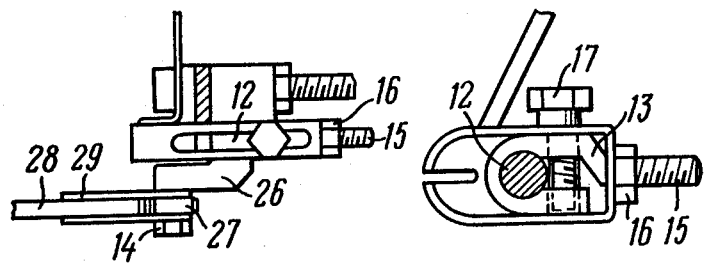
FIG. 7 is a view taken along arrow B of the hinge joint of FIG. 6.
FIG. 8 is a partly sectional view of the hinge joint taken along arrow C of FIG. 6.

In distinction from the apparatus for the surgical treatment of bones and joints considered above and shown in FIGS. 1 to 5, the apparatus shown in FIGS. 6 to 8 is intended for the treatment of polycentric joints and its construction mainly differs in a modification of the hinge joint fastening the distractors connecting the supporting and rotatable stirrups, in the shape of the regulator of the apparatus' angle of rotation, and also in the provision of an additional stirrup 25, connected to the stirrup 5 by means of straight distractors, similar to the distractos 7 and designated therefore, by the same number.

The regulator of the position of the apparatus' axis of rotation includes the pin 12 (FIGS. 7 and 8), inserted in the screw and lever-type clamp 13 and set rotatably about its own axis. Made integral with the pin is the rod 26, arranged perpendicularly to the pin's axis in the plane of rotation of the distractor 8. The regulator of the position of the axis of rotation also includes the lead screw 15 serving to move the pin 12 along the guide slots of portions 10 in the shell. Set on the free end of the rod 26 is the hinge joint for fastening the distractor 8, formed by a pinion 27 set on the fulcrum 14, which goes into an aperture in the rod 26 and engages with a toothed sector 28 on the adjoining end of the distractor 8. This type of distractor fastening is described in greater detail in the Instructions for Use of the "Apparatus for the Surgical Treatment of Joints. M. V. Volkov & O. B. Oganesyan", Moscow, 1972, USSR Ministry of Health.

The fulcrum 14, which carries the pinion 27, is connected with the toothed sector 28 of the distractor 8 through a brace 29.

The regulation of the position of the apparatus' axis of rotation is effected as follows:

After being released in the screw and lever-type clamp 13, the pin 12 is rotated, which causes the rod 26 and the fulcrum 14 to turn in the desired direction about the wire spoke 4, that direction being determined with the aid of X-ray pictures as described above. Thereafter, the pin 12 is moved by means of the lead screw 15 in the guides along the distractor's axis until the fulcrum 14 is situated in conformance with the true axis of rotation of the patient's joint, whose position is also determined by X-rays. Then the position of the pin 12 is secured with the aid of screw 17. A polycentric joint, with the apparatus mounted thereon, is exercised in the usual way, as described above, with the only difference that during the exercising of the joint, the toothed sector 28, by engaging the pinion 27, provides for kinematics characteristic of poly-centric joints. Said kinematic connection, however, as being essentially outside the subject of the present invention, will not be considered in detail.

Figure 9:
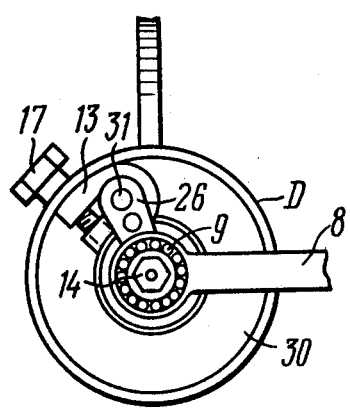
FIG. 9 shows a hinge joint mounted in a circular guide.

It should be borne in mind that several apertures may be provided on the rod 26, similar to what is further shown in FIG. 9, for regulating the radius of rotation of the hinge fulcrum 14 along a circumference in conformity with the radius of the articular ends being juxtaposed.

Figure 10:
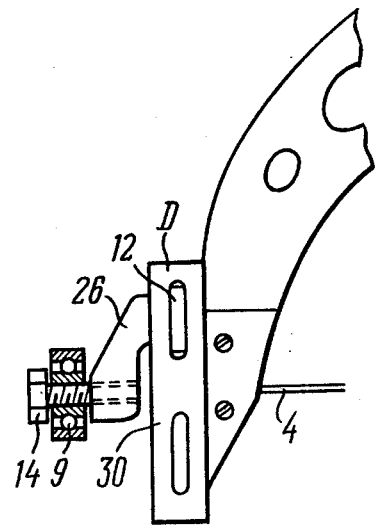
FIG. 10 shows the fastening of a hinge joint fulcrum.

Referring now to FIGS. 9 and 10, these show the hinge joint fastening the distractor 8 together with the regulator of the position of the apparatus' axis of rotation in accordance with still another embodiment of the apparatus. In this case the circular guide 30 is set coaxially with the wire spoke 4 (FIG. 10). Placed in said guide is the screw-and-lever-type clamp 13 made, in essense, similar to those described above, but having portions corresponding to the curvature of the circular guide. Mounted in the screw-and-lever-type clamp 13 is the pin 12 which is rigidly connected with the rod 26 in which there are several holes 31 for adjusting the fulcrum 14 of the hinge joint fastening the distractor.

For adjusting the position of the axis of rotation of the apparatus, the screw 17 of the screw and lever-type clamp 13 is released and, by rotating the pin about its own axis and moving the clamp 13 along the guide 30, the fulcrum 14 is brought into coincidence with the true axis of rotation of the patient's joint, determing the latter's positon, just as before, with the aid of X-ray pictures.

When using the circular guide one may provide for the permanent locking of the screw and lever-type clamp 13 in some position on the guide. For this, however, one must ensure the possibility of rotating said guide 30 about its own axis.

In this case position adjustment is effected by turning the pin 12 and the guide 30 about their own axes, as a result of which the fulcrum 14 is movable both about the wire spoke 4 and along the distractor 8, thereby taking a position at which the apparatus' axis of rotation coincides with the true axis of rotation of the patient's joint. The fulcrum 14 can be inserted in one of the holes 31, depending on the radius of the articular end.

The invention precludes damage to the articular cartilage, the hyperdistension of the capsuloligamentous apparatus of the joint and ensures better restoration of the joint's functions by providing for the possibility of aligning apparatus' axis of rotation with the true axis of rotation of the patients' joint.

What is claimed is:

1. An apparatus for the surgical treatment of bones and joints, comprising at least a supporting and a rotatable stirrups, wire spokes secured in said stirrups and intended for being drawn through juxtapositional segments of bones or joints, said rotatable stirrup and the spokes associated therewith forming a rigid system, while said supporting stirrup and the spokes associated therewith form another rigid system, distractors intended to interconnect said rigid systems, hinge joint fastenings of said distractors, situated at the two ends of the wire spoke of the supporting stirrup, the position of the axis of said hinge joint fastenings determining that of the axis of rotation of the apparatus, and a regulator of the position of the apparatus' axis of rotation, including a means for rotating the fulcrum of the hinge joint fastening of the distractors along a circumference relative to the axis of the wire spoke of said supporting stirrup, as well as a means for moving the fulcrums of the hinge joints along the distractors interconnecting said supporting and rotatable stirrups.

2. An apparatus as claimed in claim 1, wherein the means for rotating the hinge joint fulcrum is formed by a rotatable pin whose axis of rotation is parallel to the axis of the wire spoke of the supporting stirrup and which carries the fulcrum of the hinge joint, with guide slots being provided for the pin to move along the axis of the distractor interconnecting the rigid systems.

3. An apparatus as claimed in claim 2, wherein the pin has a head made flush with a disc rigidly connected with said pin and provided with an aperture for fitting therein the fulcrum of the hinge joint.

4. An apparatus as claimed in claim 2, wherein rigidly connected with said pin is a rod situated in the same plane with the distractor interconnecting the supporting and rotatable stirrups, with the fulcrum of the hinge joint being secured on said rod.

5. An apparatus as claimed in claim 2, wherein connected with said pin is a lead screw for moving said pin in the guide slots along the distractor interconnecting the supporting and rotatable stirrups of the rigid systems, with a screw and lever-type clamp being provided for securing the pin in the desired position after movement.

6. An apparatus as claimed in claim 3, wherein said disc has several holes arranged at different radial distances from the pin's axis of rotation and serving to alter the radius of the rotation of the hinge joint fulcrum relative to the wire spoke in conformity with the radius of the surfaces of the segments being juxtaposed.

7. An apparatus as claimed in claim 4, wherein said rod has several apertures arranged at different distances from said pin's axis of rotation and serving to alter the radius of the rotation of the hinge joint fulcrum relative to the wire spoke in conformity with the radius of the surfaces of the segments being juxtaposed.

8. An apparatus as claimed in claim 1, wherein sid regulator of the position of the apparatus' axis of rotation is formed by a circular guide whose center coincides with the axis of the wire spoke of the supporting stirrup, and set in said guide rotatably about its own axis and movably therein is a pin carrying a rod rigidly connected therewith and situtated in the plane of rotation of the distractor interconnecting the supporting and rotatable stirrups, and provided with a hole for setting therein the fulcrum of the hinge joint fastening the distractors.

9. An apparatus as claimed in claim 1, wherein the regulator of the position of the apparatus' axis of rotation is formed by a circular guide whose center coincides with the axis of the wire spoke of the supporting stirrup, and set in said guide rotatably about its own axis is a pin carrying a rod rigidly connected thereto and provided with an aperture for securing the fulcrum of the hinge joint, while said guide is set rotatably about its own axis.

10. An apparatus as claimed in claim 9, wherein said rod has a number of holes for setting the pin at different distances from the center of the circular guide.

* * * * *